(12) United States Patent
Brunsgaard et al.

(10) Patent No.: US 6,293,930 B1
(45) Date of Patent: Sep. 25, 2001

(54) LOW-PROFILE OSTOMY FACEPLATE WITH RECESSED COUPLING RING

(75) Inventors: Poul H. Brunsgaard; Ronald S. Botten, both of Gurnee, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 09/249,561

(22) Filed: Feb. 12, 1999

Related U.S. Application Data

(63) Continuation-in-part of application No. 09/095,991, filed on Jun. 11, 1998, now Pat. No. 6,093,276.

(51) Int. Cl.[7] .................................................. A61F 5/44
(52) U.S. Cl. .......................... 604/322; 604/336; 604/337; 604/338; 604/342
(58) Field of Search .................................. 604/332, 336, 604/337, 338, 339, 342, 344; 156/219; 424/443–446

(56) References Cited

U.S. PATENT DOCUMENTS

| 4,610,676 | * | 9/1986 | Schneider et al. | 604/339 |
| 4,775,374 | | 10/1988 | Cilento et al. | 604/344 |
| 5,026,360 | * | 6/1991 | Johnsen et al. | 604/338 |
| 5,088,992 | * | 2/1992 | Edwards et al. | 604/338 |
| 5,185,008 | | 2/1993 | Lavender | 604/338 |
| 5,501,677 | * | 3/1996 | Jensen | 604/338 |
| 5,607,413 | * | 3/1997 | Holmberg et al. | 604/342 |
| 5,609,585 | * | 3/1997 | Botten et al. | 604/332 |
| 5,716,475 | * | 2/1998 | Botten et al. | 156/219 |
| 5,730,736 | * | 3/1998 | Sawers et al. | 604/344 |
| 5,834,009 | * | 11/1998 | Sawers et al. | 424/443 |
| 5,947,941 | * | 9/1999 | Leise, Jr. et al. | 604/338 |

FOREIGN PATENT DOCUMENTS

| 0611123A | | 8/1994 | (EP) . |
| 1031334 | * | 1/2000 | (EP) . |
| 2290974A | | 1/1996 | (GB) . |
| 2299510A | | 9/1996 | (GB) . |

\* cited by examiner

*Primary Examiner*—Kim M. Lewis
(74) *Attorney, Agent, or Firm*—Marshall, O'Toole, Gerstein, Murray & Borun

(57) ABSTRACT

An ostomy faceplate for a two-piece appliance is disclosed in which the coupling ring is partially recessed into the wafer of the faceplate. The wafer includes a hydrocolloid-containing adhesive layer that is provided with a recess that receives a portion of the coupling ring, thereby resulting in a faceplate of distinctively low profile and enhanced conformability.

17 Claims, 1 Drawing Sheet

LOW-PROFILE OSTOMY FACEPLATE WITH RECESSED COUPLING RING

RELATED APPLICATION

This application is a continuation-in-part of application Ser. No. 09/095,991, filed Jun. 11, 1998 now U.S. Pat. No. 6,093,276.

BACKGROUND AND SUMMARY

Co-pending application Ser. No. 09/095,991 discloses an ostomy appliance faceplate with a concealed coupling ring flange and an in-line method for manufacturing such a product. Such an appliance is one component of a two-piece appliance, the other component being a collection pouch having a flexible plastic coupling ring capable of being mated with and disconnected from the coupling ring of the faceplate. The faceplate includes not only a flexible plastic coupling ring, typically with an attachment flange, but also a multi-layer adhesive wafer joined to the faceplate coupling ring. The wafer includes a layer of moisture-absorbing adhesive skin barrier material having a bodyside surface covered by a removable release sheet and an opposite surface covered by a thin, flexible (and preferably elastomeric) backing film. The flange of the coupling ring is secured to the backing film by heat-sealing or by other suitable means.

In the aforementioned co-pending application, a flexible cover layer extends over the front surface of the flange of the coupling ring and the surface of the backing film located radially outwardly beyond the flange. Therefore, the flange is sandwiched between the cover layer and the film of the wafer. The advantages are partly aesthetic since such construction enhances the low-profile appearance of the faceplate assembly and provides an unbroken surface extending from the coupling portion of the ring all the way to the outer periphery of the faceplate. However, the construction also has functional advantages since it protects the edge portions of the coupling ring's flange from pulling away from the film of the wafer (or vice versa), prevents liquids or particulates from entering the space between the periphery of the flange and the film, and enhances the security of attachment between the flange and the backing film of the wafer.

Co-pending application Ser. No. 09/095,991 discloses an in-line method for making ostomy faceplates in which all operations are carried out simultaneously and continuously to yield finished products, thereby eliminating problems and expenses of handling, storage, and transfer commonly associated with prior manufacturing techniques utilizing extrusion processes. It has been found that the injection/compression molding method is particularly amenable to coordination with automated production of other components, resulting in a combination of in-line operations in which the assembling procedures are integrated with the molding, forming, cutting, and other parts-making operations to provide a continuity of automated steps culminating in the production of finished products. Most advantageously, therefore, the faceplates of this invention may be produced by the method of the co-pending application. Alternatively, the faceplates of this invention may be made by other procedures and processes well known in the art.

An important aspect of the present invention lies in the discovery that the advantages of a faceplate having the features disclosed in said co-pending application may be greatly increased if the front or pouchside surface of the wafer is recessed to receive a portion of the flexible coupling ring, thereby substantially reducing the thickness of the faceplate in the area of the coupling ring. The result is a faceplate of extremely low profile which, when mated with the ring of a pouch, results in a two-piece ostomy appliance that is flatter, less conspicuous, and more comfortable to wear than the faceplates of two-piece appliances known heretofore. Furthermore, since such coupling rings are designed to flex in use, thereby complying with body movements and external forces, the relative thinness of the wafer lying directly beneath and supporting the faceplate coupling ring promotes even greater flexibility of the ring in use and further reduces the possibility that unintentional coupling might occur. Where such a faceplate coupling ring is provided with an attachment flange, the pouch-facing surface of that flange preferably lies along the same plane as the adjacent surface of the wafer, resulting in a construction in which the flange is concealed and protected against exposure to forces that might otherwise tend to pry it away from the wafer. Such advantages are particularly apparent where a flexible cover layer (preferably of soft non-woven material) extends over both the flange and the surface of the wafer adjacent to the flange, thereby completely concealing and embedding the flange beneath the flat unbroken surface of the cover layer.

Other features, objects and advantages of the invention will become apparent from the drawings and specification.

DRAWINGS

DETAILED DESCRIPTION OF PREFERRED EMBODIMENTS

Figure 1:
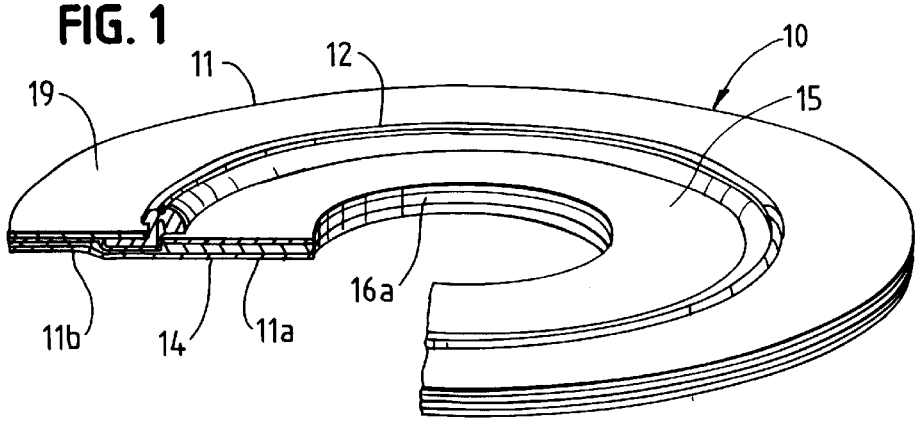
FIG. 1 is a partial perspective view of an ostomy faceplate embodying the invention.
Figure 2:
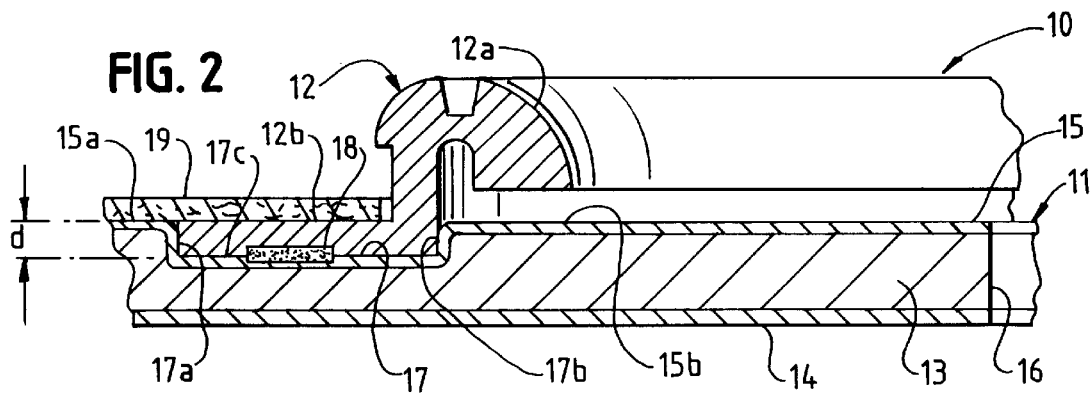
FIG. 2 is a greatly enlarged fragmentary sectional view of the faceplate of FIG. 1.

Referring to FIGS. 1 and 2, the numeral 10 generally designates a faceplate for a two-piece ostomy appliance. The faceplate as shown is generally circular in outline, but other shapes, such as oval or generally rectangular with rounded corners, may be provided. The faceplate includes a wafer 11 and a coupling ring 12. As shown most clearly in FIG. 2, the wafer comprises a layer 13 of moisture-absorbing adhesive skin barrier material having a bodyside surface covered by a removable release sheet 14 and an opposite surface covered by a thin backing layer 15.

The term "skin barrier" is widely used in the medical field, and is used herein, to refer to any of a variety of materials in which a soft, sticky, and pliant adhesive composition constitutes a continuous phase and particles of one or more liquid-absorbing and swellable hydrocolloids are dispersed throughout the adhesive and constitute a discontinuous phase. The adhesive phase contains at least one elastomer such as polyisobutylene, often in combination with one or more tackifiers, plasticizers, and antioxidants. An elastomer such as a styrene-isoprene-styrene block copolymer (e.g., "Cariflex" TR-1107, from Shell Chemical Co.) or a styrene-butadiene-styrene block copolymer (e.g., "Kraton" 1100 Series from Shell Chemical Co.) may be included, and other ABA block copolymers, such as ethylene-propylene block copolymers known as EPR rubbers have also been included in adhesive compositions for increasing the elastomeric properties of such barrier materials.

The discontinuous phase may be particles of any suitable hydrocolloid or mixtures of hydrocolloids such as sodium carboxymethylcellulose, calcium, carboxymethylcellulose, pectin, gelatin, and natural gums such as guar gum, gum arabic, locust bean gum, karaya, and the like. Such hydrocolloids are water-absorbing and water-swellable. They absorb moisture from the skin and contribute to the wet-tack characteristics of the skin barrier material, all as well known in the art.

As shown in FIG. 1, wafer 11 may be contoured, having a relatively thick central body portion 11a and a thinner peripheral flange portion 11b. The thickness of the body portion increases the moisture absorbing capacity of the wafer and promotes an effective seal directly around a patient's stoma, whereas the thinness of the peripheral portion enhances flexibility and compliance with the skin and reduces the possibility that channeling and leakage might occur. While such contouring is considered highly advantageous, it is nevertheless optional and, if desired, the barrier thickness of the peripheral portion 11b may be the same as, or even greater than, the thickness of body portion 11a surrounding stoma opening 16.

The removable release sheet 14 along the bodyside surface of the wafer is formed of any suitable material that is tough, flexible, and substantially non-stretchable. Siliconized paper may be used effectively. A polymeric material, such as polyethylene therephthalate, is particularly desirable because of its high tensile strength and transparency, but other thermoplastic materials having similar properties may be used. An anti-stick coating of silicone may be provided on the release sheet and, if desired, a tab portion of the release sheet may project beyond the skin barrier layer 13 to facilitate removal of the release sheet when the faceplate is to be adhered to the skin.

The backing layer 15 is composed of a heat-sealable material that is flexible and preferably elastomeric. A film of polyurethane is believed particularly effective but other polymeric films having similar properties may be used. Further, the backing layer may be formed of a heat-sealable non-woven fabric which is preferably porous but not necessarily so. One such material that is believed particularly effective for this purpose is a breathable (i.e., gas-transmissible) non-woven fabric composed of spunbonded or meltblown thermoplastic fibers. A spunbonded low-density polyethylene non-woven fabric available under the designation "Daltex" 6080-A1-UPE from Don & Low Ltd., Forfar, Scotland is believed suitable, but other soft, porous, heat-sealable non-woven fabrics are available and may be used. Flexible and resilient thermoplastic foam materials of open or semi-open cell structure are also believed suitable for fabrication of backing layer 15.

Wafer 11, including adhesive layer 13, backing layer 15, and release sheet 14, is provided with a central opening 16 to serve as a starter opening which may then be enlarged (by cutting with scissors) to match the shape and size of a patient's stoma. Alternatively, the central opening may be pre-sized to eliminate the need for cutting at the time of application.

The coupling ring 12 of the faceplate, like that of the coupling ring of the pouch (not shown), may be formed of low-density polyethylene or other flexible thermoplastic material having similar properties. Typically, the faceplate coupling ring has an annular coupling portion 12a, shown in FIG. 2 as a male element capable of being received by and coupling with the female element (not shown) of a pouch, and an attachment portion 12b in the form of a radially outwardly extending flange for attachment to wafer 11. The particular coupling ring illustrated in FIGS. 1 and 2 is similar to the ring shown and described in co-owned U.S. Pat. No. 5,185,008, the disclosure of which is incorporated by reference herein. It is to be understood, however, the details of connecting portion 12a are not critical to the present invention and that a ring having a connecting portion of somewhat different construction and operation may be provided. What is significant is that the annular connecting portion 12a should project axially away from the wafer, extend about a stoma-receiving opening 16, and be adapted for mechanically coupling to a second ring provided by an ostomy pouch.

Wafer 11 has its pouchside surface provided with a recess 17 which, as shown in FIG. 2, is dimensioned to receive a portion of coupling ring 12, specifically, the flange portion 12b of that coupling ring. The depth "d" of the recess, which is lined by backing layer 15, corresponds to the thickness of the flange portion 12b so that the top surface of the flange portion is flush with at least one adjacent surface 15a of the wafer.

As depicted in FIG. 2, recess 17 has a pair of concentric annular side surfaces 17a and 17b that are normal to the plane of the wafer and a base surface 17c parallel with and below that of wafer surfaces 15a and 15b adjoining recess 17. The flange 12b of the coupling ring is securely affixed to the base surface 17 by any suitable means, most desirably by a heat seal 18 welding the flange to the thermoplastic backing layer 15 within the recess. A flexible covering layer 19, preferably of soft non-woven fabric, extends over the pouch side surface of flange 12b and the co-planar adjoining surface 15a of the wafer, thereby completely concealing the flange within the recess of the wafer.

The flange is therefore effectively embedded within the wafer with the result that faceplate 10 is of distinctively low profile with its flange portion anchored and concealed within the recess of the wafer. Such a construction also has important functional advantages since it protects the peripheral edge portion of flange 12b and enhances the security of attachment between the coupling ring and the wafer. Also, the reduced thickness of the barrier material beneath the base of the recess is considered advantageous because the greater flexibility of the barrier layer in that area tends to offset at least partially the decrease in flexibility occasioned by the presence of flange portion 12b.

Cover layer 19 may be formed of any of a variety of flexible and stretchable materials. Most advantageously, it is composed of a soft, flexible and stretchable fabric, particularly a non-woven fabric such as spunbonded, low-density polyethylene fabric available under the designation "Daltex" 6080-A1-UPE from Don & Low Ltd., Forfar, Scotland. Other materials having somewhat similar properties that might be used include flexible and resilient polymeric foam materials of either open or closed cell structure. A pressure sensitive adhesive coating upon the bodyside surface of cover layer 19 secures that layer to both the flange 12b and the surface 15a of the backing layer adjoining recess 17.

Figure 3:
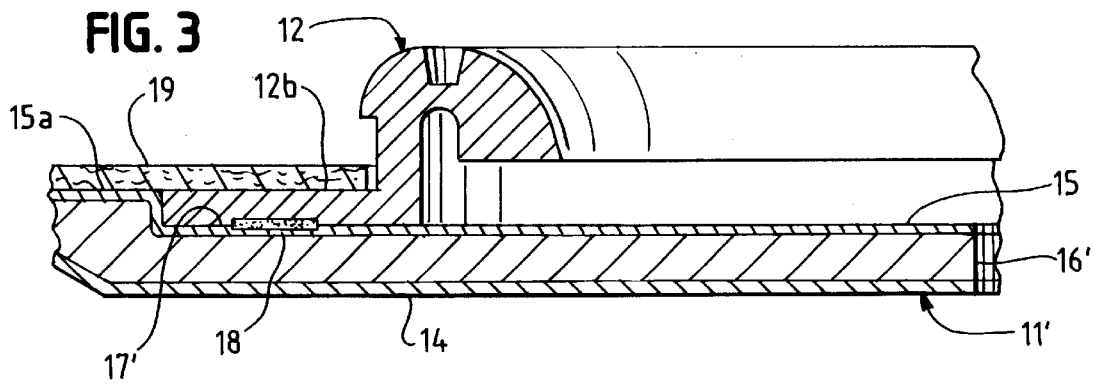
FIG. 3 is an enlarged sectional view similar to FIG. 2 but illustrating a second embodiment of the invention.

The embodiment of FIG. 3 is similar to the one already described except that the thickness of the wafer 11' within the outline of coupling ring 12 is of substantially the same thickness as the portion of the wafer beneath flange 12b. The recess 17' therefore extends radially inwardly all the way to stoma-receiving opening 16'. Such a construction may be considered desirable where greater flexibility of that portion of the wafer inboard of the coupling ring is an objective and where high absorbency of the barrier layer about the edges of the stoma-receiving opening 16' is regarded as of lesser importance.

Figure 4:
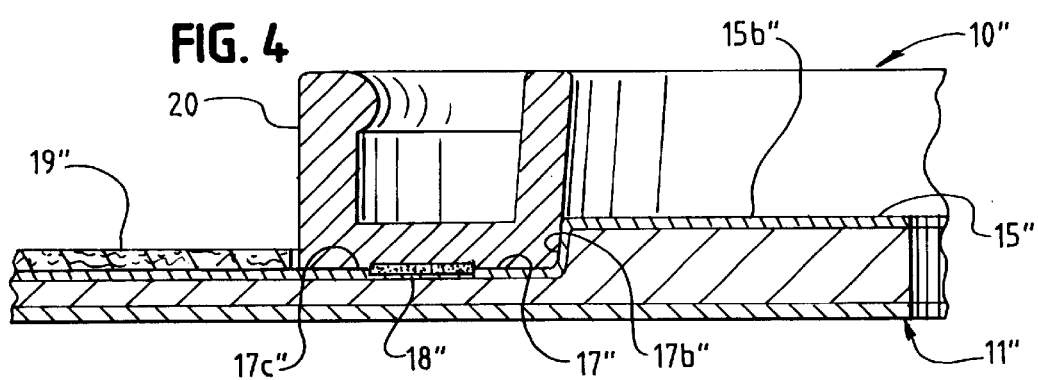
FIG. 4 is a sectional view of a third embodiment.

As previously noted, the male coupling rings 12 of the embodiments already described are designed to mate with female coupling rings mounted on collection pouches (not shown). The arrangement may be reversed with the female ring provided by the faceplate and the male ring mounted on a pouch. The embodiment of FIG. 4 therefore depicts a faceplate 10" in which a female coupling ring 20 of annular channel-shaped configuration is secured to wafer 11". The wafer is recessed at 17" below adjoining surface 15". While in this embodiment the wafer has only one side surface 17$b''$ normal to base surface 17$c''$, it is to be understood that the thickness of the barrier material outboard of the coupling ring might be increased to provide the recess with a second side surface corresponding to surface 17$a$ of the FIG. 2 embodiment. In any event, it is important that the coupling ring, whether male or female, be partially embedded within a recess formed in the pouchside surface of wafer 11, 11', or 11", that the recess include a base surface to which the coupling ring is secured, preferably by heat seal 18 or 18", and that the recess be defined by at least one side surface that extends generally normal to the plane of the wafer.

While in the foregoing we have disclosed embodiments of the invention in considerable detail for purposes of illustration, it will be understood by those skilled in the art that many of these details may be varied without departing from the spirit and scope of the invention.

What is claimed is:

1. A faceplate for a two-piece ostomy appliance, said faceplate comprising a coupling ring for mechanically and detachably coupling said faceplate to a collection pouch and an adhesive wafer supporting said coupling ring for adhesively joining said faceplate to the peristomal skin surfaces of a patient; said wafer being generally planar and including a layer of hydrocolloid-containing adhesive skin barrier material; wherein the improvement comprises said wafer having a recess facing in the direction of said coupling ring and having at least one side surface generally normal to the plane of said wafer; said wafer also having a base surface extending along a plane below that of a surface of said wafer adjoining said recess; said coupling ring including a portion thereof received in said recess and secured to the said base surface of said recess beneath the plane of said adjoining surface.

2. The faceplate of claim 1 in which said wafer includes a thermoplastic backing layer along the surface thereof facing said coupling ring.

3. The faceplate of claim 2 in which said backing layer extends into said recess and along the base surface thereof.

4. The faceplate of claim 3 in which said coupling ring is heat sealed to said backing layer along the base surface of said recess.

5. The faceplate of claim 1 in which said coupling ring is a male coupling ring.

6. The faceplate of claim 1 in which said coupling ring is a female coupling ring.

7. The faceplate of claim 1 in which said skin barrier layer extends beneath said base surface of said coupling ring and has a thickness substantially less than the thickness of said barrier layer beneath said adjoining surface.

8. The faceplate of claim 7 in which said wafer includes surface portions facing said coupling ring and disposed inboard and outboard of said coupling ring; said adjoining surface being disposed outboard of said coupling ring.

9. The faceplate of claim 7 in which said wafer includes surface portions facing in the direction of said coupling ring and disposed inboard and outboard of said coupling ring; said adjoining surface being disposed inboard of said coupling ring.

10. The faceplate of claim 7 in which said wafer includes surface portions facing said coupling ring and disposed inboard and outboard of said coupling ring; said inboard surface being located both inboard and outboard of said coupling ring.

11. The faceplate of claims 8, 9 or 10 in which said wafer includes a backing layer covering said skin barrier layer and extending over said base surface in said recess; said backing layer being secured to said skin barrier layer by the adhesiveness of said skin barrier layer; said coupling ring being affixed to said backing layer within said recess.

12. The faceplate of claim 11 in which said backing layer and said coupling ring are each formed of thermoplastic heat-sealable material; said coupling ring being heat-sealed to said backing layer within said recess.

13. A faceplate for two-piece ostomy appliance, said faceplate comprising the coupling ring for mechanically and detachably coupling said faceplate to a collection pouch and an adhesive wafer supporting said coupling ring for adhesively joining said faceplate to the peristomal skin surfaces of a patient; said wafer being generally planar and including a layer of hydrocolloidal-containing adhesive skin barrier material; said coupling ring including an annular connecting portion extending axially away from said wafer and a radially outwardly extending flange portion extending along the plane of said wafer; wherein the improvement comprises said wafer having a recess facing in the direction of said coupling ring and receiving the flange portion thereof; said wafer having a surface adjoining said recess that is flush with a surface of said flange facing away from said recess; and means securing said flange to said wafer within said recess.

14. The faceplate of claim 13 in which said wafer includes a backing layer covering said skin barrier layer and extending into said recess; said backing layer being secured to said skin barrier layer by the adhesiveness of said skin barrier layer; said flange portion of said coupling ring being affixed to said backing layer within said recess.

15. The faceplate of claim 14 in which said backing layer and said coupling ring are each formed of thermoplastic heat-sealable material; said flange portion of said coupling ring being heat-sealed to said backing layer within said recess.

16. The faceplate of claims 13, 14 or 15 in which an annular covering layer extends about said coupling ring and covers both said flange portion and the adjacent surface of said wafer extending thereabout.

17. The faceplate of claim 16 in which said covering layer is formed of soft fabric and is adhesively secured to both said flange portion and said adjoining surface.

* * * * *